US008422706B2

(12) United States Patent
Kulkarni et al.

(10) Patent No.: US 8,422,706 B2
(45) Date of Patent: Apr. 16, 2013

(54) METHODS AND SYSTEMS FOR REDUCING AN EFFECT OF AMBIENT NOISE WITHIN AN AUDITORY PROSTHESIS SYSTEM

(75) Inventors: Abhijit Kulkarni, Newbury Park, CA (US); Leonid M. Litvak, Los Angeles, CA (US); Aniket Saoji, Newhall, CA (US)

(73) Assignee: Advanced Bionics, LLC, Valencia, CA (US)

( * ) Notice: Subject to any disclaimer, the term of this patent is extended or adjusted under 35 U.S.C. 154(b) by 284 days.

(21) Appl. No.: 12/879,603

(22) Filed: Sep. 10, 2010

(65) Prior Publication Data

US 2011/0064241 A1 Mar. 17, 2011

Related U.S. Application Data

(60) Provisional application No. 61/241,472, filed on Sep. 11, 2009.

(51) Int. Cl.
*H04R 25/00* (2006.01)
*H04B 15/00* (2006.01)

(52) U.S. Cl.
USPC .......................................... 381/317; 381/94.1

(58) Field of Classification Search ................. 381/23.1, 381/71.1, 71.6, 94.1, 94.7, 312, 317, 318, 381/320, 321, 323, 328; 607/55
See application file for complete search history.

(56) References Cited

U.S. PATENT DOCUMENTS

| | | | |
|---|---|---|---|
| 7,251,530 | B1 | 7/2007 | Overstreet et al. |
| 2005/0209657 | A1 | 9/2005 | Chung et al. |
| 2006/0287609 | A1 | 12/2006 | Litvak et al. |
| 2010/0185261 | A1 | 7/2010 | Schleich |

FOREIGN PATENT DOCUMENTS

| | | |
|---|---|---|
| EP | 0326905 | 8/1989 |

OTHER PUBLICATIONS

International Search Report and Written Opinion received in International Application No. PCT/US2010/048503 dated Dec. 28, 2010.

*Primary Examiner* — Tuan D Nguyen
(74) *Attorney, Agent, or Firm* — ALG Intellectual Property, LLC

(57) ABSTRACT

An exemplary method of reducing an effect of ambient noise within an auditory prosthesis system includes dividing an audio signal presented to an auditory prosthesis patient into a plurality of analysis channels each containing a frequency domain signal representative of a distinct frequency portion of the audio signal, determining a signal-to-noise ratio and a noise reduction gain parameter based on the signal-to-noise ratio for each of the frequency domain signals, applying noise reduction to the frequency domain signals in accordance with the determined noise reduction gain parameters to generate a noise reduced frequency domain signal corresponding to each of the analysis channels, and generating one or more stimulation parameters based on the noise reduced frequency domain signals and in accordance with at least one of a current steering stimulation strategy and an N-of-M stimulation strategy. Corresponding methods and systems are also disclosed.

20 Claims, 10 Drawing Sheets

METHODS AND SYSTEMS FOR REDUCING AN EFFECT OF AMBIENT NOISE WITHIN AN AUDITORY PROSTHESIS SYSTEM

RELATED APPLICATIONS

The present application claims priority under 35 U.S.C. §119(e) to U.S. Provisional Patent Application No. 61/241,472 by Abhijit Kulkarni et al., filed on Sep. 11, 2009, and entitled "Methods and Systems for Reducing an Effect of Ambient Noise Within a Cochlear Implant System," the contents of which are hereby incorporated by reference in their entirety.

BACKGROUND INFORMATION

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Many auditory prosthesis patients report difficulty hearing in noisy environments. For example, ambient noise within a particular listening environment may adversely affect a listening experience for an auditory prosthesis patient by diminishing the ability of the patient to perceive audio signals of interest. Hence, noise reduction within an auditory prosthesis system is desirable. One solution that has been proposed is to process an incoming audio signal with noise reduction circuitry contained with a traditional hearing aid before the audio signal is presented to an auditory prosthesis system. However, this solution involves a great amount of redundant computation, is cumbersome for the patient, and is expensive to implement.

SUMMARY

An exemplary method of reducing an effect of ambient noise within an auditory prosthesis system includes dividing an audio signal presented to an auditory prosthesis patient into a plurality of analysis channels each containing a frequency domain signal representative of a distinct frequency portion of the audio signal, determining a noise reduction gain parameter for each of the frequency domain signals, applying noise reduction to the frequency domain signals in accordance with the determined noise reduction gain parameters to generate a noise reduced frequency domain signal corresponding to each of the analysis channels, and generating one or more stimulation parameters based on the noise reduced frequency domain signals and in accordance with at least one of a current steering stimulation strategy and an N-of-M stimulation strategy.

An exemplary system for reducing an effect of ambient noise within an auditory prosthesis system includes a frequency analysis facility configured to a divide an audio signal presented to an auditory prosthesis patient into a plurality of analysis channels each containing a frequency domain signal representative of a distinct frequency portion of the audio signal, a noise reduction facility communicatively coupled to the analysis channel facility and configured to determine a noise reduction gain parameter for each of the frequency domain signals and apply noise reduction to the frequency domain signals in accordance with the determined noise reduction gain parameters to generate a noise reduced frequency domain signal corresponding to each of the analysis channels, and a stimulation strategy facility communicatively coupled to the noise reduction facility and configured to generate one or more stimulation parameters based on the noise reduced frequency domain signals and in accordance with at least one of a current steering stimulation strategy and an N-of-M stimulation strategy.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
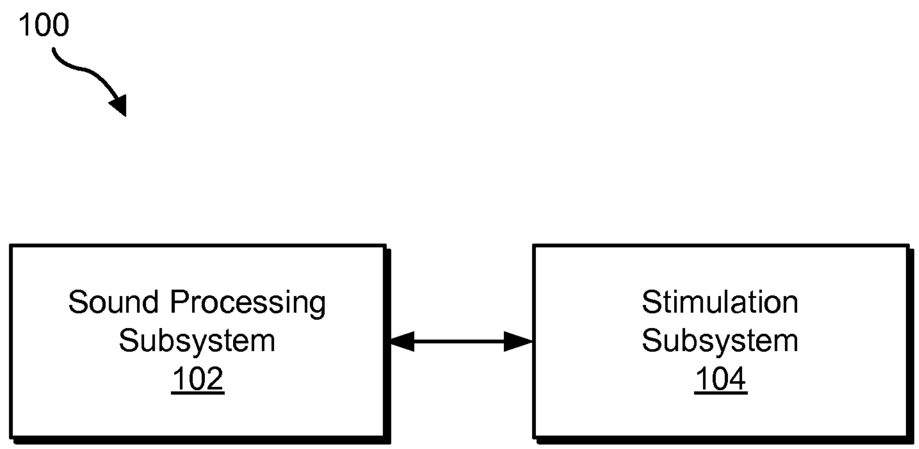
FIG. 1 illustrates an exemplary auditory prosthesis system according to principles described herein.

Methods and systems for reducing an effect of ambient noise within an auditory prosthesis system are described herein. In some examples, an audio signal presented to an auditory prosthesis patient is divided into a plurality of analysis channels each containing a frequency domain signal representative of a distinct frequency portion of the audio signal. A noise reduction gain parameter based, e.g., on the signal-to-noise ratio for each of the frequency domain signals may then be determined. Noise reduction may be applied to the frequency domain signals in accordance with the determined noise reduction gain parameters to generate a noise reduced frequency domain signal corresponding to each of the analysis channels. One or more stimulation parameters based on the noise reduced frequency domain signals may be generated in accordance with at least one of a current steering stimulation strategy and an N-of-M stimulation strategy.

As used herein, a "current steering stimulation strategy" is one in which weighted stimulation current is applied concurrently to two or more electrodes by an auditory prosthesis (e.g., an implantable cochlear stimulator) in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes. Current steering may be used for any other reason as may serve a particular application and will be described in more detail below.

As used herein, an "N-of-M stimulation strategy" is one in which stimulation current is only applied to N of M total stimulation channels during a particular stimulation frame, where N is less than M. An N-of-M stimulation strategy may be used to prevent irrelevant information contained within an audio signal from being presented to an auditory prosthesis user, achieve higher stimulation rates, minimize electrode interaction, and/or for any other reason as may serve a particular application. Exemplary N-of-M stimulation strategies will be described in more detail below.

Application of one or more of the noise reduction heuristics described herein to an audio signal in conjunction with at least one of a current steering stimulation strategy and an N-of-M stimulation strategy may result in an enhanced listening experience for an auditory prosthesis patient located in an environment that includes ambient noise. For example, noise reduction in conjunction with a current steering stimulation strategy and/or an N-of-M stimulation strategy may result in enhanced spectral resolution, more accurate conveyance of information contained within an audio signal, and/or optimal speech recognition.

In some examples, once an audio signal has been transformed into the frequency domain, the methods described herein may be performed entirely within in the frequency domain. In this manner, re-synthesis of the audio signal (i.e., conversion of the audio signal back into the time domain) does not have to be performed. In this manner, the signal processing resources needed to perform the methods described herein may be minimized.

FIG. 1 illustrates an exemplary auditory prosthesis system 100. As shown in FIG. 1, auditory prosthesis system 100 may include a sound processing subsystem 102 and a stimulation subsystem 104 configured to communicate with one another. As will be described in more detail below, auditory prosthesis system 100 may be configured to reduce perception of ambient noise by an auditory prosthesis patient by applying a noise reduction heuristic to an audio signal and applying electrical stimulation representative of the noise reduced audio signal to at least one stimulation site within a patient in accordance with at least one of a current steering stimulation strategy and an N-of-M stimulation strategy.

Sound processing subsystem 102 may be configured to detect or sense an audio signal and divide the audio signal into a plurality of analysis channels each containing a frequency domain signal (or simply "signal") representative of a distinct frequency portion of the audio signal. Sound processing subsystem 102 may be further configured to determine a signal-to-noise ratio ("SNR") and a noise reduction gain parameter based on the signal-to-noise ratio for each of the frequency domain signals within the analysis channels and apply noise reduction to the frequency domain signals in accordance with the determined noise reduction gain parameters to generate a noise reduced frequency domain signal corresponding to each of the analysis channels. Sound processing subsystem 102 may be further configured to generate one or more stimulation parameters based on the noise reduced frequency domain signals and in accordance with at least one of a current steering stimulation strategy and an N-of-M stimulation strategy. Sound processing subsystem 102 may then transmit the one or more stimulation parameters to stimulation subsystem 104.

Stimulation subsystem 104 may be configured to generate and apply electrical stimulation (also referred to herein as "stimulation current" and/or "stimulation pulses") to one or more stimulation sites associated with an auditory pathway (e.g., the auditory nerve) of a patient in accordance with one or more stimulation parameters transmitted thereto by sound processing subsystem 102. Exemplary stimulation sites include, but are not limited to, one or more locations within the cochlea, the cochlear nucleus, the inferior colliculus, and/or any other nuclei in the auditory pathway. The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

Figure 2:
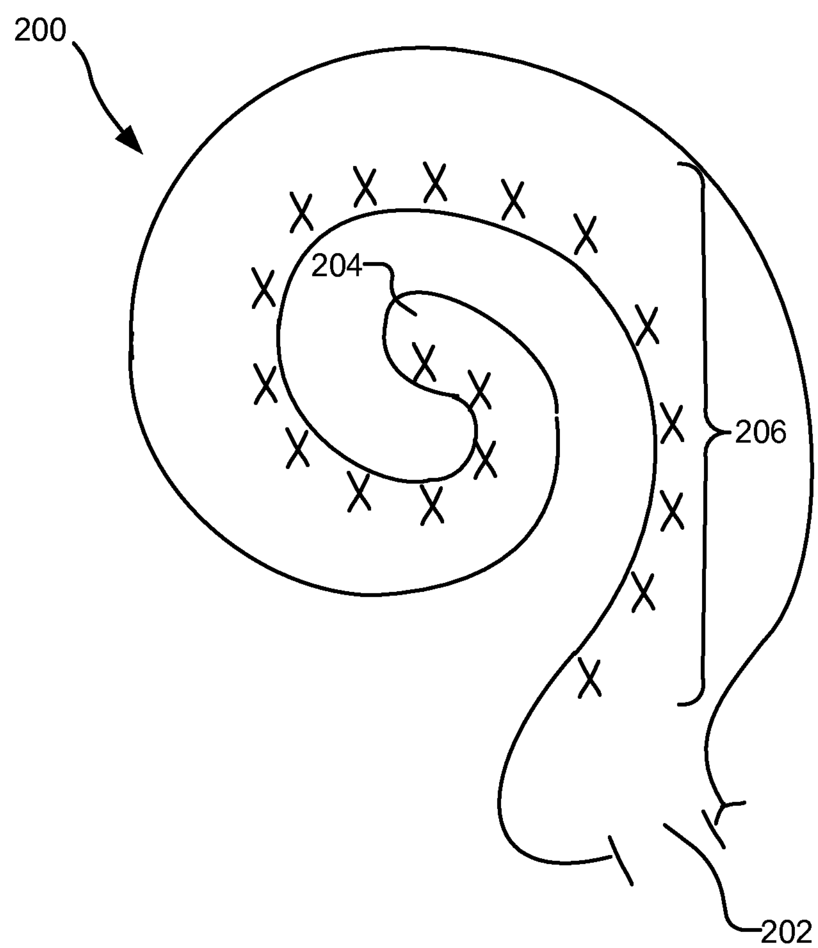
FIG. 2 illustrates a schematic structure of the human cochlea according to principles described herein.

As mentioned, the one or more stimulation sites to which electrical stimulation is applied may include any target area or location within the cochlea. FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 104 may therefore be configured to apply electrical stimulation to different locations within the cochlea 200 (e.g., different locations along the auditory nerve tissue 206) to provide a sensation of hearing.

Returning to FIG. 1, sound processing subsystem 102 and stimulation subsystem 104 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

Auditory prosthesis system 100, including sound processing subsystem 102 and stimulation subsystem 104, may include any hardware, computer-implemented instructions (e.g., software), firmware, or combinations thereof configured to perform one or more of the processes described herein. For example, auditory prosthesis system 100, including sound processing subsystem 102 and stimulation subsystem 104, may include hardware (e.g., one or more signal processors and/or other computing devices) configured to perform one or more of the processes described herein.

One or more of the processes described herein may be implemented at least in part as instructions executable by one or more computing devices. In general, a processor receives instructions from a computer-readable medium (e.g., a memory, etc.) and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computing device (e.g., by a processor within sound processing subsystem 102). Such a medium may take many forms, including, but not limited to, non-volatile media and/or volatile media. Exemplary computer-readable media that may be used in accordance with the systems and methods described herein include, but are not limited to, random access memory ("RAM"), dynamic RAM, a PROM, an EPROM, a FLASH-EEPROM, any other memory chip or cartridge, or any other medium from which a computing device can read.

Figure 3:
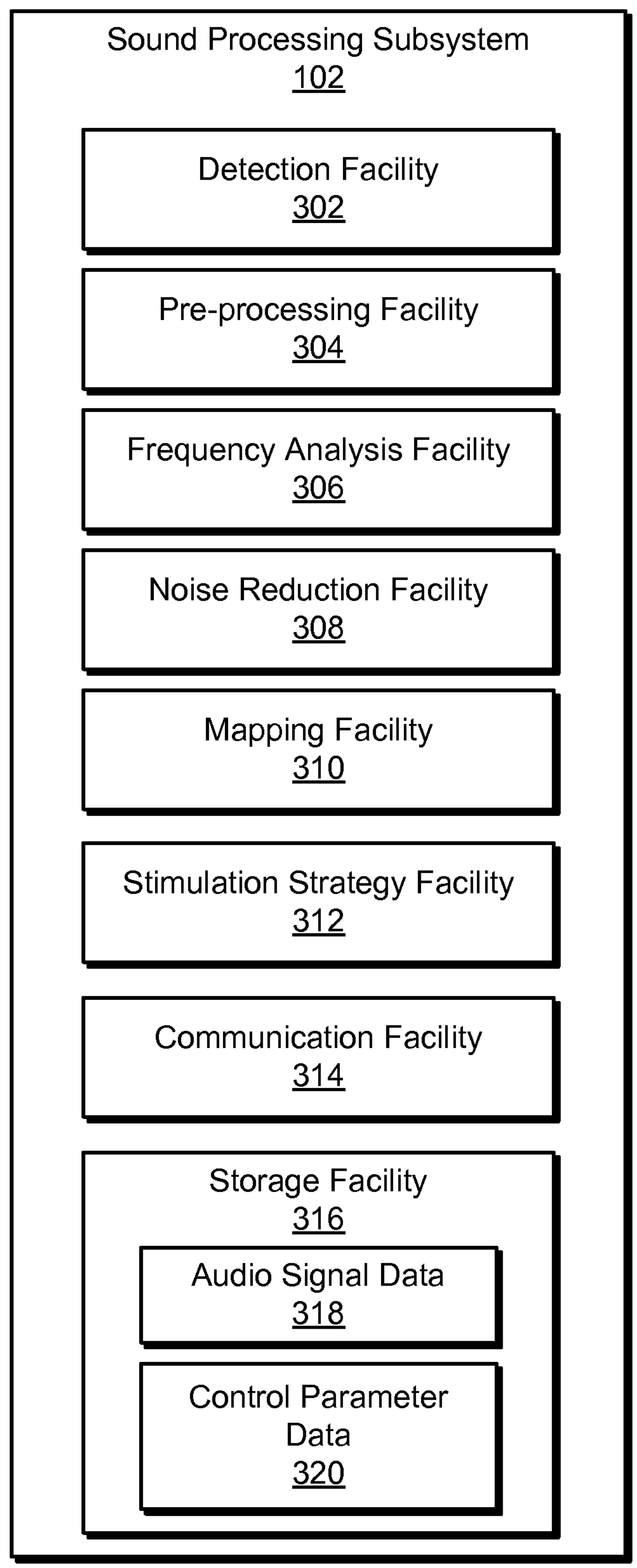
FIG. 3 illustrates exemplary components of a sound processing subsystem according to principles described herein.

FIG. 3 illustrates exemplary components of sound processing subsystem 102. As shown in FIG. 3, sound processing subsystem 102 may include a detection facility 302, a pre-processing facility 304, a frequency analysis facility 306, a noise reduction facility 308, a mapping facility 310, a stimulation strategy facility 312, a communication facility 314, and a storage facility 316, which may be in communication with one another using any suitable communication technologies. Each of these facilities 302-316 may include any combination of hardware, software, and/or firmware as may serve a particular application. For example, one or more of facilities 302-316 may include a computing device or processor configured to perform one or more of the functions described herein. Facilities 302-316 will now be described in more detail.

Detection facility 302 may be configured to detect or sense one or more audio signals and convert the detected signals to corresponding electrical signals. To this end, detection facility 302 may include a microphone or other transducer. In some examples, the one or more audio signals may include speech. The one or more audio signals may additionally or alternatively include music, ambient noise, and/or other sounds.

Pre-processing facility 304 may be configured to perform various signal processing operations on the one or more audio signals detected by detection facility 302. For example, pre-processing facility 304 may amplify a detected audio signal, convert the audio signal to a digital signal, filter the digital signal with a pre-emphasis filter, subject the digital signal to automatic gain control, and/or perform one or more other signal processing operations on the detected audio signal.

Frequency analysis facility 306 may be configured to divide the audio signal into a plurality of analysis channels each containing a frequency domain signal representative of a distinct frequency portion of the audio signal. For example, frequency analysis facility 306 may include a plurality of band-pass filters configured to divide the audio signal into a plurality of frequency channels or bands. Additionally or alternatively, frequency analysis facility 306 may be configured to convert the audio signal from a time domain into a frequency domain and then divide the resulting frequency bins into the plurality of analysis channels. To this end, frequency analysis facility 206 may include one or more components configured to apply a Discrete Fourier Transform (e.g., a Fast Fourier Transform ("FFT")) to the audio signal.

Frequency analysis facility 306 may be configured to divide the audio signal into any number of analysis channels as may serve a particular application. In some examples, the total number of analysis channels is set to be less than or equal to a total number of stimulation channels through which electrical stimulation representative of the audio signal is applied to an auditory prosthesis patient.

Noise reduction facility 308 may be configured to apply noise reduction to the signals within the analysis channels in accordance with any suitable noise reduction heuristic as may serve a particular application. For example, as will be described in more detail below, noise reduction facility 308 may be configured to generate a noise reduction gain parameter for each of the signals within the analysis channels and apply noise reduction to the signals in accordance with the determined noise reduction gain parameters.

In some examples, noise reduction facility 308 may be further configured to dynamically adjust an amount of noise reduction applied to the signals within the analysis channels in accordance with the type of audio signal presented to the auditory prosthesis patient. For example, noise reduction facility 308 may be configured to detect that an audio signal comprises music, in which case noise reduction facility 308 may be configured to reduce or minimize the amount of noise reduction applied to the signals within the analysis channels. This is because music and other types of audio signals are best presented to an auditory prosthesis patient with little or no noise reduction.

Mapping facility 310 may be configured to map the noise reduced signals within the analysis channels to electrical stimulation pulses to be applied to a patient via one or more stimulation channels. For example, signal levels of the noise reduced signals within the analysis channels are mapped to amplitude values used to define electrical stimulation pulses that are applied to the patient by stimulation subsystem 104 via one or more corresponding stimulation channels. Mapping facility 310 may be further configured to perform additional processing of the noise reduced signals contained within the analysis channels, such as signal compression.

Stimulation strategy facility 312 may be configured to generate one or more stimulation parameters based on the noise reduced signals within the analysis channels and in accordance with one or more stimulation strategies. Exemplary stimulation strategies include, but are not limited to, a current steering stimulation strategy and an N-of-M stimulation strategy. Exemplary current steering stimulation strategies and N-of-M stimulation strategies will be described in more detail below.

Communication facility 314 may be configured to facilitate communication between sound processing subsystem 102 and stimulation subsystem 104. For example, communication facility 314 may include one or more coils configured to transmit control signals (e.g., the one or more stimulation parameters generated by stimulation strategy facility 312) and/or power via one or more communication links to stimulation subsystem 104. Additionally or alternatively, communication facility 314 may one or more wires or the like that are configured to facilitate direct communication with stimulation subsystem 104.

Storage facility 316 may be configured to maintain audio signal data 318 representative of an audio signal detected by detection facility 302 and control parameter data 320 representative of one or more control parameters, which may include one or more stimulation parameters to be transmitted from sound processing subsystem 102 to stimulation subsystem 104. Storage facility 316 may be configured to maintain additional or alternative data as may serve a particular application.

Figure 4:
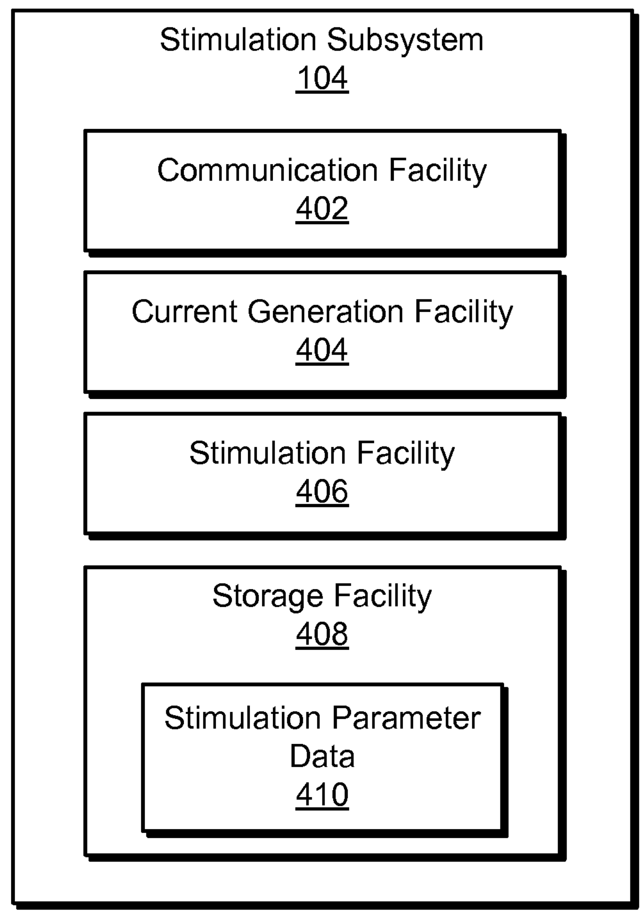
FIG. 4 illustrates exemplary components of a stimulation subsystem according to principles described herein.

FIG. 4 illustrates exemplary components of stimulation subsystem 104. As shown in FIG. 4, stimulation subsystem 104 may include a communication facility 402, a current generation facility 404, a stimulation facility 406, and a storage facility 408, which may be in communication with one another using any suitable communication technologies. Each of these facilities 402-408 may include any combination of hardware, software, and/or firmware as may serve a particular application. For example, one or more of facilities 402-408 may include a computing device or processor configured to perform one or more of the functions described herein. Facilities 402-408 will now be described in more detail.

Communication facility 402 may be configured to facilitate communication between stimulation subsystem 104 and sound processing subsystem 102. For example, communication facility 402 may include one or more coils configured to receive control signals and/or power via one or more communication links to stimulation subsystem 104. Communication facility 402 may additionally or alternatively be configured to transmit one or more status signals and/or other data to sound processing subsystem 102.

Current generation facility 404 may be configured to generate electrical stimulation in accordance with one or more stimulation parameters received from sound processing subsystem 102. To this end, current generation facility 404 may include one or more current generators and/or any other circuitry configured to facilitate generation of electrical stimulation.

Stimulation facility 406 may be configured to apply the electrical stimulation generated by current generation facility 404 to one or more stimulation sites within the cochlea of a patient in accordance with the one or more stimulation strategies selected by stimulation strategy facility 312. To this end, as will be illustrated in more detail below, stimulation facility 406 may include one or more electrodes disposed on a lead that may be inserted within the cochlea, into one or more nuclei in the auditory pathway (e.g., into the cochlear nucleus and/or the inferior colliculus), and/or at any other location along the auditory pathway.

Storage facility 408 may be configured to maintain stimulation parameter data 410 as received from sound processing subsystem 102. Stimulation parameter data 410 may be representative of one or more stimulation parameters configured to define the electrical stimulation generated and applied by stimulation subsystem 104. Storage facility 408 may be configured to maintain additional or alternative data as may serve a particular application.

Figure 5:
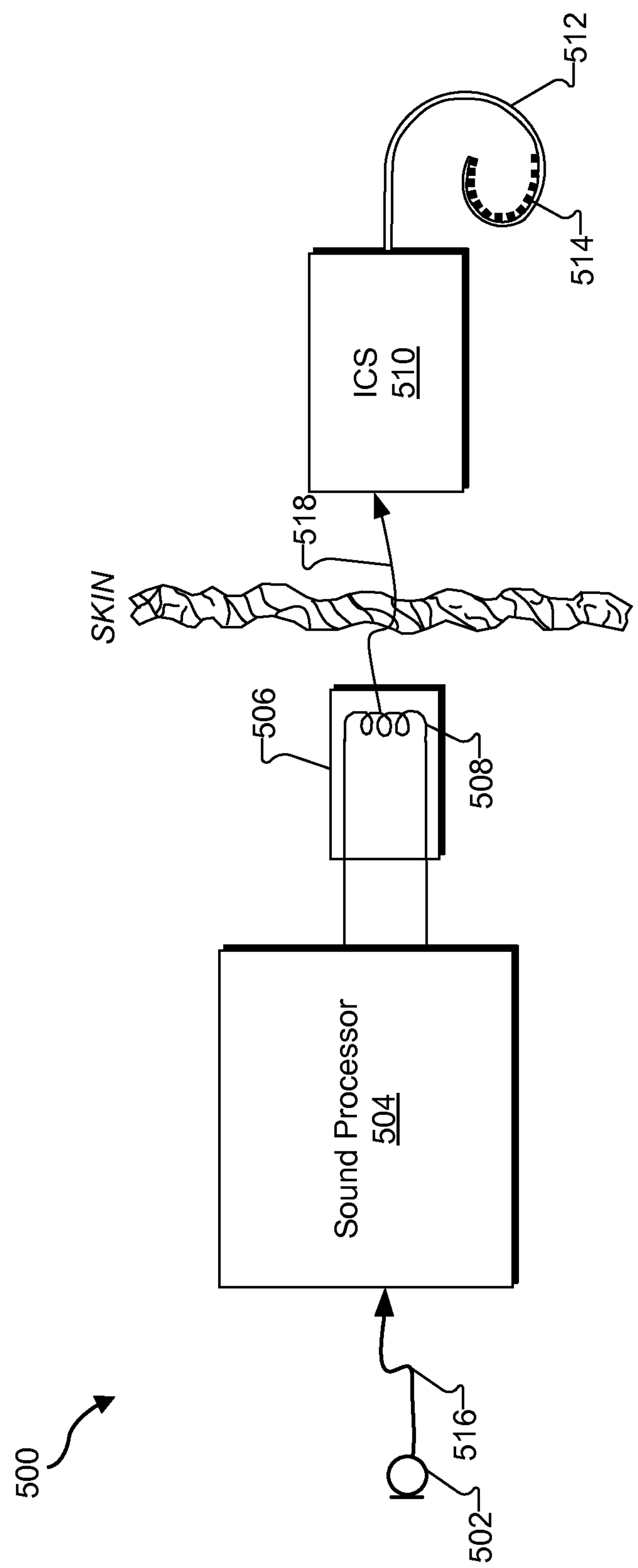
FIG. 5 illustrates an exemplary cochlear implant system according to principles described herein.

FIG. 5 illustrates an exemplary cochlear implant system 500, which may implement auditory prosthesis system 100. It will be recognized that cochlear implant system 500 is one of many different types of systems that may implement auditory prosthesis system 100. For example, in some alternative implementations, a brainstem implant and/or any other type of auditory prosthesis may be implanted within a patient and configured to apply stimulation to one or more stimulation sites located along an auditory pathway of a patient.

As shown in FIG. 5, cochlear implant system 500 may include a microphone 502, a sound processor 504, a headpiece 506 having a coil 508 disposed therein, an implantable cochlear stimulator ("ICS") 510, a lead 512, and a plurality of electrodes 514 disposed on the lead 512. Additional or alternative components may be included within cochlear implant system 500 as may serve a particular application. The facilities described herein may be implemented by or within one or more components shown within FIG. 5. For example, detection facility 302 may be implemented by microphone 502. Pre-processing facility 304, frequency analysis facility 306, noise reduction facility 308, mapping facility 310, stimulation strategy facility 312, and/or storage facility 316 may be implemented by sound processor 504. Communication facility 314 may be implemented by headpiece 506 and coil 508. Communication facility 402, current generation facility 404, and storage facility 408 may be implemented by implantable cochlear stimulator 508. Stimulation facility 406 may be implemented by lead 510 and electrodes 512.

As shown in FIG. 5, microphone 502, sound processor 504, and headpiece 506 may be located external to a patient. In some alternative examples, microphone 502 and/or sound processor 504 may be implanted within the patient. In such configurations, the need for headpiece 506 may be obviated.

Microphone 502 may detect an audio signal and convert the detected signal to a corresponding electrical signal. Microphone 502 may be placed external to the patient, within the ear canal of the patient, or at any other suitable location as may serve a particular application. The electrical signal may be sent from microphone 502 to sound processor 504 via a communication link 514, which may include a telemetry link, a wire, and/or any other suitable communication link.

Sound processor 504 is configured to process the converted audio signal in accordance with a selected sound processing strategy to generate appropriate stimulation parameters for controlling implantable cochlear stimulator 510. Sound processor 504 may include or be implemented within a behind-the-ear ("BTE") unit, a portable speech processor ("PSP"), and/or any other sound processing unit as may serve a particular application. Exemplary components of sound processor 504 will be described in more detail below.

Sound processor 504 may be configured to transcutaneously transmit data (e.g., data representative of one or more stimulation parameters) to implantable cochlear stimulator 504 via coil 508. As shown in FIG. 5, coil 508 may be housed within headpiece 506, which may be affixed to a patient's head and positioned such that coil 508 is communicatively coupled to a corresponding coil (not shown) included within implantable cochlear stimulator 510. In this manner, data may be wirelessly transmitted between sound processor 504 and implantable cochlear stimulator 510 via communication link 518. It will be understood that data communication link 118 may include a bi-directional communication link and/or one or more dedicated uni-directional communication links. In some alternative embodiments, sound processor 504 and implantable cochlear stimulator 510 may be directly connected with one or more wires or the like.

Implantable cochlear stimulator 510 may be configured to generate electrical stimulation representative of an audio signal detected by microphone 502 in accordance with one or more stimulation parameters transmitted thereto by sound processing subsystem 102. Implantable cochlear stimulator 510 may be further configured to apply the electrical stimulation to one or stimulation sites within the cochlea via one or more electrodes 514 disposed along lead 512.

To facilitate application of the electrical stimulation generated by implantable cochlear stimulator 510, lead 512 may be inserted within a duct of the cochlea such that electrodes 514 are in communication with one or more stimulation sites within the cochlea. As used herein, the term "in communication with" refers to electrodes 514 being adjacent to, in the general vicinity of, in close proximity to, directly next to, or directly on the stimulation site. Any number of electrodes 514 (e.g., sixteen) may be disposed on lead 512 as may serve a particular application.

Figure 6:
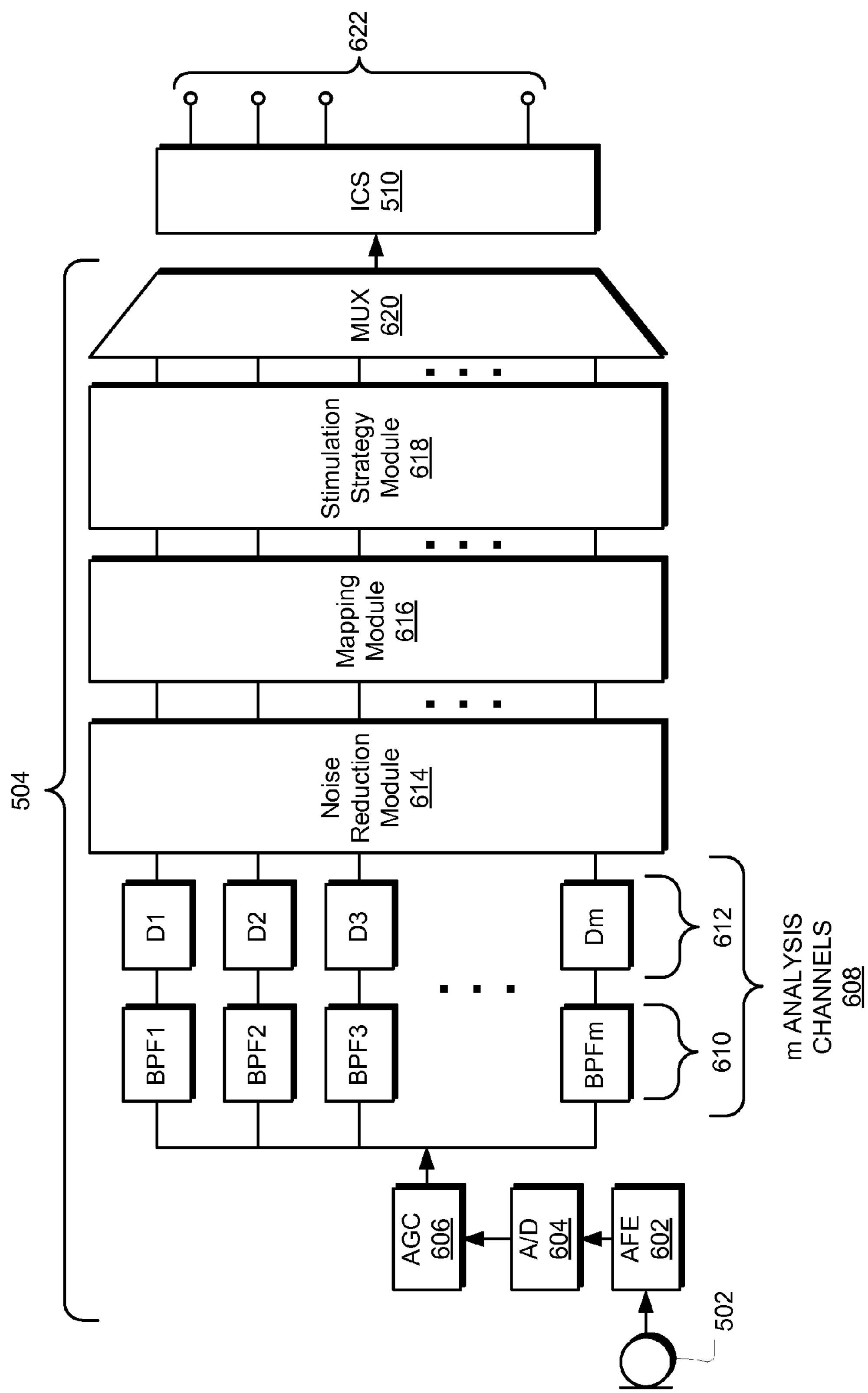
FIG. 6 illustrates components of an exemplary sound processor coupled to an implantable cochlear stimulator according to principles described herein.

FIG. 6 illustrates components of an exemplary sound processor 504 coupled to an implantable cochlear stimulator 510. The components shown in FIG. 6 may be configured to perform one or more of the processes associated with one or more of the facilities 302-316 associated with sound processing subsystem 102 and are merely representative of the many different components that may be included within sound processor 504.

As shown in FIG. 6, microphone 502 senses an audio signal, such as speech or music, and converts the audio signal into one or more electrical signals. These signals are then amplified in audio front-end ("AFE") circuitry 602. The amplified audio signal is then converted to a digital signal by an analog-to-digital ("A/D") converter 604. The resulting digital signal is then subjected to automatic gain control using a suitable automatic gain control ("AGC") unit 606.

After appropriate automatic gain control, the digital signal is subjected to a plurality of filters 610 (e.g., a plurality of band-pass filters). Filters 610 are configured to divide the digital signal into m analysis channels 608 each containing a signal representative of a distinct frequency portion of the audio signal sensed by microphone 502. Additional or alternative components may be used to divide the signal into the analysis channels 608 as may serve a particular application. For example, as described previously, one or more components may be included within sound processor 504 that are configured to apply a Discrete Fourier Transform to the audio signal and then divide the resulting frequency bins into the analysis channels 608.

As shown in FIG. 6, the signals within each analysis channel 608 may be input into an energy detector 612. Each energy detector 612 may include any combination of circuitry configured to detect an amount of energy contained within each of the signals within the analysis channels 608. For example, each energy detector 612 may include a rectification circuit followed by an integrator circuit.

After energy detection, the signals within the m analysis channels 608 are input into a noise reduction module 614. Noise reduction module 614 may perform one or more of the functions described in connection with noise reduction facility 308. For example, noise reduction module 614 may generate a noise reduction gain parameter for each of the signals within analysis channels 608 based on a signal-to-noise ratio of each respective signal and apply noise reduction to the signals in accordance with the determined noise reduction gain parameters. Noise reduction module 614 will be described in more detail below.

Mapping module 616 may perform one or more of the functions described in connection with mapping facility 310. For example, mapping module 616 may map the signals in the analysis channels 608 to one or more stimulation channels after the signals have been subjected to noise reduction by noise reduction module 614. For example, signal levels of the noise reduced signals generated by noise reduction module 614 are mapped to amplitude values used to define the electrical stimulation pulses that are applied to the patient by implantable cochlear stimulator 510 via M stimulation channels 622. In some examples, groups of one or more electrodes 514 may make up the M stimulation channels 622.

Stimulation strategy module 618 may perform one or more of the functions described in connection with stimulation strategy facility 312. For example, stimulation strategy module 618 may generate one or more stimulation parameters based on the noise reduced signals and in accordance with one or more stimulation strategies. To illustrate, stimulation strategy module 618 may be configured to generate one or more stimulation parameters that direct implantable cochlear stimulator 510 to generate and concurrently apply weighted stimulation current via a plurality of stimulation channels 622 in order to effectuate a current steering stimulation strategy. Stimulation strategy module 618 may additionally or alternatively be configured to generate one or more stimulation parameters that direct implantable cochlear stimulator 510 to apply electrical stimulation via only a subset of stimulation channels 622 in order to effectuate an N-of-M stimulation strategy.

Multiplexer 620 may be configured to serialize the stimulation parameters generated by stimulation strategy module 618 so that they can be transmitted to implantable cochlear stimulator 510 via coil 508. The implantable cochlear stimulator 510 may then generate and apply electrical stimulation via one or more of the M stimulation channels 622 to one or more stimulation sites within the duct of the patient's cochlea in accordance with the one or more stimulation parameters.

Figure 7:
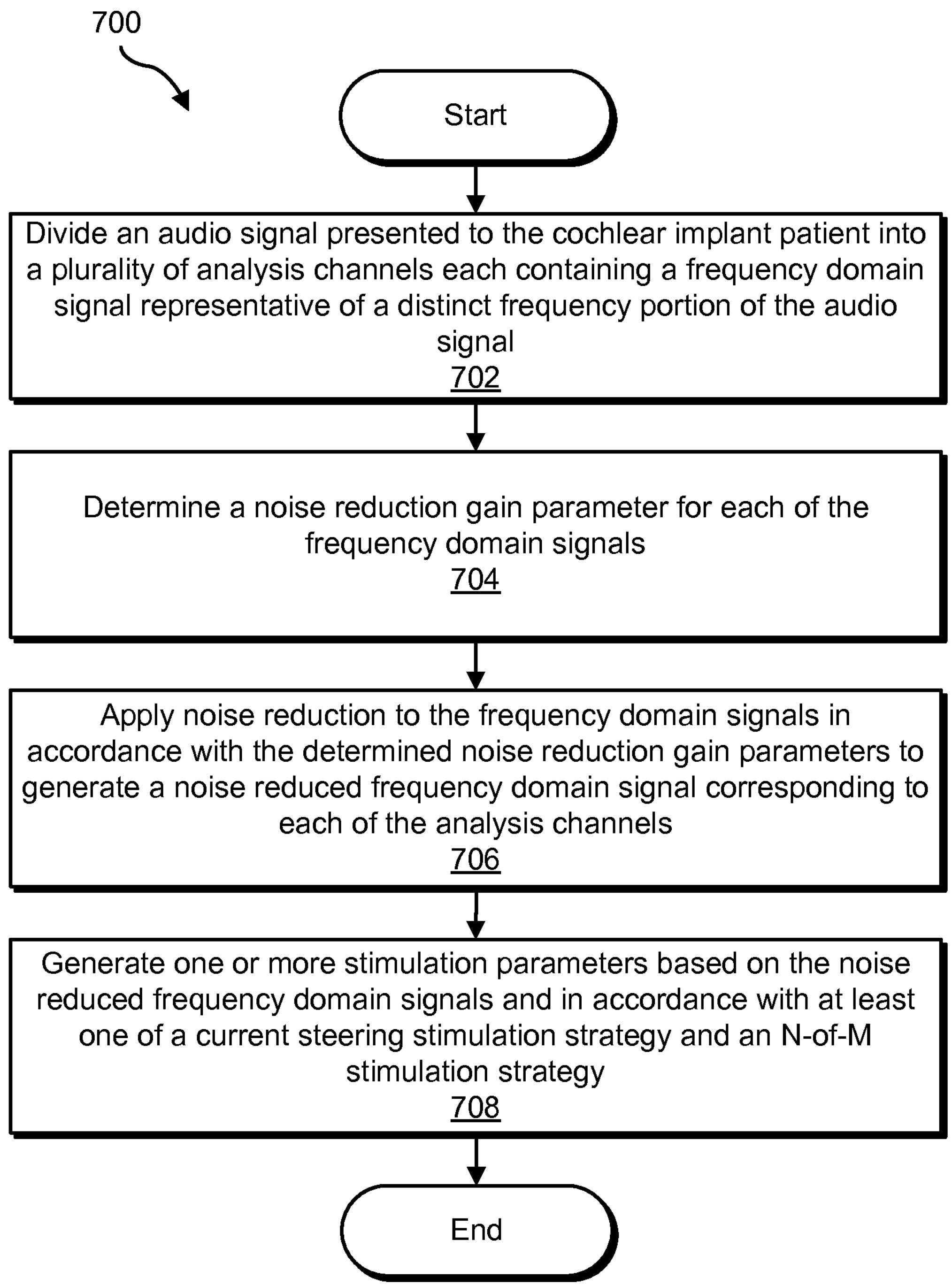
FIG. 7 illustrates an exemplary method of reducing an effect of ambient noise within an auditory prosthesis system according to principles described herein.

FIG. 7 illustrates an exemplary method 700 of reducing an effect of ambient noise within an auditory prosthesis system. While FIG. 7 illustrates exemplary steps according to one embodiment, other embodiments may omit, add to, reorder, and/or modify any of the steps shown in FIG. 7. It will be recognized that any of the systems, subsystems, facilities, and/or modules described herein may be configured to perform one or more of the steps shown in FIG. 7.

In step 702, an audio signal presented to an auditory prosthesis patient is divided into a plurality of analysis channels each containing a frequency domain signal representative of a distinct frequency portion of the audio signal. Step 702 may be performed by frequency analysis facility 306, for example, in any of the ways described herein.

In step 704, a noise reduction gain parameter is determined for each of the frequency domain signals provided in step 702. The noise reduction gain parameter for each of the frequency domain signals may be determined in any of the ways described herein. For example, the noise reduction gain parameter for each of the frequency domain signals may be based on a signal-to-noise ratio of each of the frequency domain signals.

Figure 8:
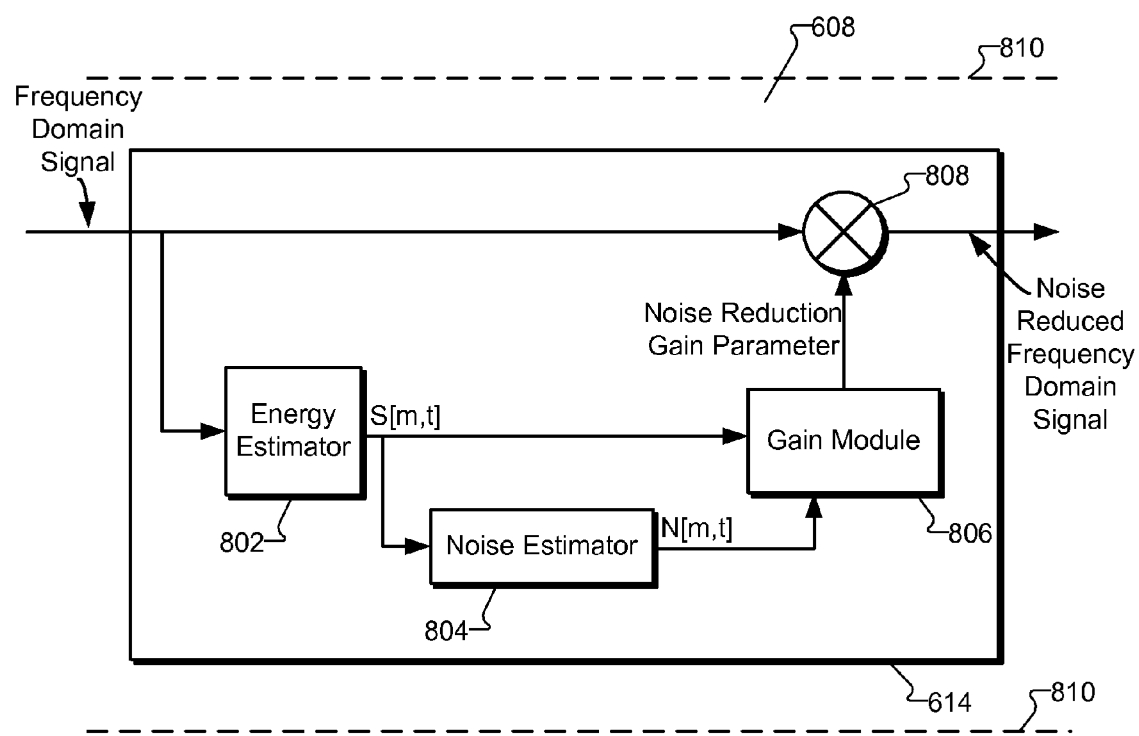
FIG. 8 shows exemplary components that may be included within a noise reduction module according to principles described herein.

To illustrate, FIG. 8 shows exemplary components that may be included within noise reduction module 614 that may be used to determine a signal-to-noise ratio and a noise reduction gain parameter for a frequency domain signal within a particular analysis channel 608. As shown in FIG. 8, noise reduction module 614 may include an energy estimator 802, a noise estimator 804, a gain module 806, and a multiplication block 808 communicatively coupled to one another.

Energy estimator 802, noise estimator 804, gain module 806, and multiplication block 808 are included within dashed lines 810 to illustrate that they are specific to a particular analysis channel 608. Hence, in some examples, each of these components 802-808 may be replicated for each analysis channel 608. In some examples, a single component (e.g., a digital signal processor) or combination of components may be configured to perform the functions associated with each of the components 802-808 for each of the signals contained within analysis channels 608.

As shown in FIG. 8, energy estimator 802 may be configured to estimate or otherwise determine a signal level (also referred to as an energy level) of a frequency domain signal contained within a particular analysis channel 608. The signal level may be estimated in any suitable manner as may serve a particular application. The signal level of the frequency domain signal contained within analysis channel 608 may be represented as S[m,t], where m represents the particular analysis channel number and t represents time. Hence, S[m,t] represents the signal level estimate of the signal in channel m at time t.

The estimated signal level is input into noise estimator 804, which analyzes the estimated energy level to determine an estimated noise level of the signal. The estimated noise level may be determined in any suitable manner as may serve a particular application and may be represented as N[m,t], where m represents the particular analysis channel number and t represents time. Hence, N[m,t] represents the noise level estimate in channel m at time t.

Gain module 806 may be configured to accept both S[m,t] and N[m,t] and determine a noise reduction gain parameter based on the signal level and the noise level of the signal contained within analysis channel 608. For example, gain module 806 may take the ratio of S[m,t] to N[m,t] to determine a signal-to-noise ratio ("SNR") of the signal contained within analysis channel 608, which may be represented by SNR[m,t]. Gain module 806 may then determine a noise reduction gain parameter based on the signal-to-noise ratio of the frequency domain signal (i.e., SNR[m,t]). The noise reduction gain parameter may be determined based on any suitable heuristic. For example, the noise reduction gain parameter may be determined using a predetermined gain function as shown in Equation 1:

$$G_{NR}[m,t]=F(SNR[m,t]) \quad \text{(Equation 1)}$$

The gain function shown in Equation 1 may be implemented in any suitable manner as may serve a particular application. To illustrate, the gain function may be implemented as a look up table configured to assign a particular noise reduction gain parameter to a frequency domain signal based on the signal-to-noise ratio of the frequency domain signal. For example, a noise reduction gain parameter may have any value between 0 and 1. If the signal-to-noise ratio of a particular frequency domain signal above a predetermined maximum threshold (i.e., the noise level within the signal is comparatively low), the noise reduction gain parameter may be set to 1. In this manner, as will be described in more detail below, when the noise reduction gain parameter is applied to the frequency domain signal by multiplication block 808, no attenuation of the frequency domain signal is performed. Conversely, if the signal-to-ratio of a particular frequency domain signal is below a predetermined minimum threshold (i.e., the noise level within the signal is comparatively high), the noise reduction gain parameter may be set to 0. In this manner, as will be described in more detail below, when the noise reduction gain parameter is applied to the frequency domain signal by multiplication block 808, the frequency domain signal is completely attenuated, thereby reducing the amount of ambient noise perceived by a patient. Values between 0 and 1 may be assigned to frequency domain signals having signal-to-noise ratios between the predetermined minimum and maximum thresholds as may serve a particular application.

In some examples, the predetermined minimum and maximum thresholds against which the signal-to-noise ratios are compared may be independently set for each analysis channel 308. Hence, each analysis channel 308 may have different values for its corresponding predetermined minimum and maximum thresholds as compared with the other analysis channels 308. The predetermined minimum and maximum thresholds for each analysis channel 308 may be determined in any suitable manner as may serve a particular application.

It will be recognized that the noise reduction gain parameter determined by gain module 806 may be based on any other input as may serve a particular application. For example, the noise reduction gain parameter determined by gain module 806 may be based on only the noise level of the frequency domain signal within analysis channel 308 and/or on any other suitable input.

Returning to FIG. 7, in step 706, noise reduction is applied to the frequency domain signals in accordance with the noise reduction gain parameters determined in step 704 to generate a noise reduced frequency domain signal corresponding to each of the analysis channels. For example, as shown in FIG. 8, the frequency domain signal and the noise reduction gain parameter generated by gain module 806 for analysis channel 608 may both be input into multiplication block 808, which may be configured to multiply the frequency domain signal by the noise reduction gain parameter. In this manner, gain equal to the value of the noise reduction gain parameter may be applied to the frequency domain signal to produce a noise reduced frequency domain signal. As used herein, a "noise reduced frequency domain signal" refers to a frequency domain signal after a noise reduction gain parameter has been applied thereto. It will be recognized that if the noise reduction gain parameter is equal to 1, the noise reduced frequency domain signal may be substantially the same as the frequency domain signal. It will be recognized that noise reduced frequency domain signals corresponding to other analysis channels 308 may be generated in a similar manner.

In step 708, one or more stimulation parameters based on the noise reduced frequency domain signals are generated in accordance with at least one of a current steering stimulation strategy and an N-of-M stimulation strategy. Exemplary implementations of a current steering stimulation strategy and an N-of-M stimulation strategy will now be described.

Figure 9:
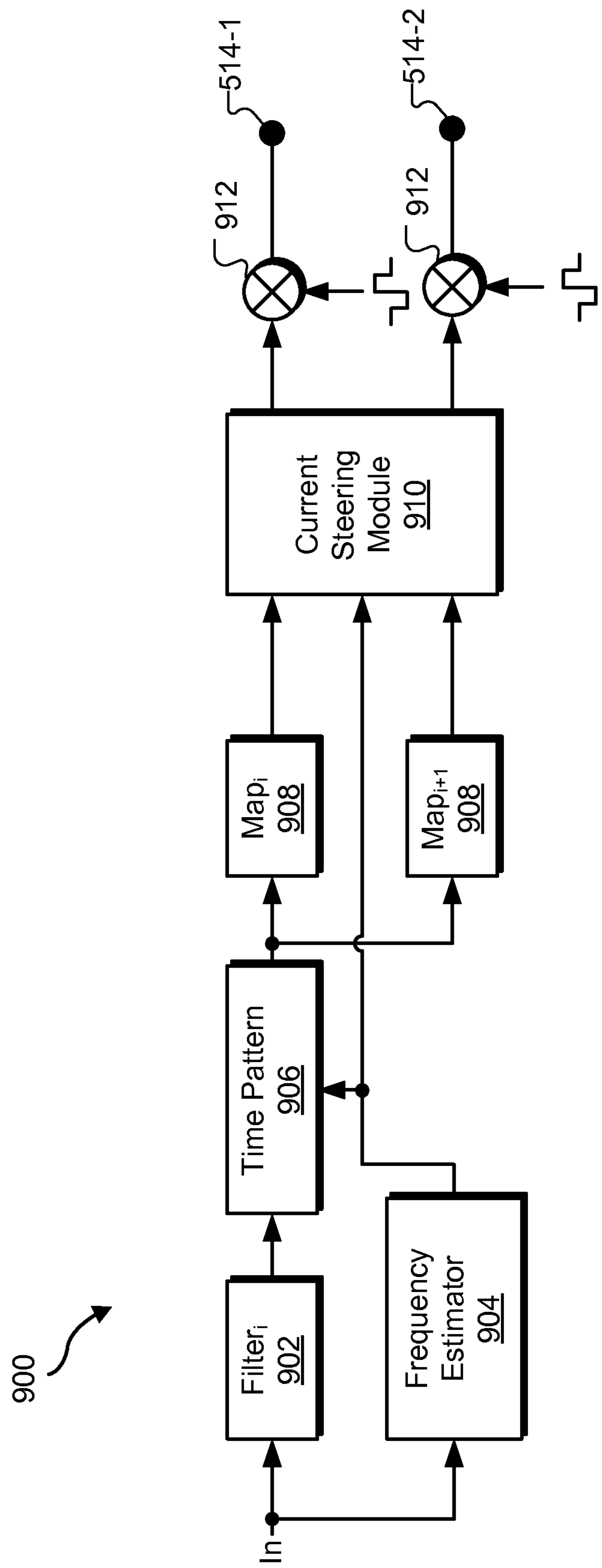
FIG. 9 illustrates an exemplary implementation of a current steering strategy according to principles described herein.

FIG. 9 illustrates an exemplary implementation 900 of a current steering strategy. As mentioned above, current steering may be used to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes. Current steering may be used for any other reason as may serve a particular application and will be described in more detail below.

The components and functions illustrated in FIG. 9 may be implemented by any of the subsystems, facilities, and/or modules described herein. For examples, one or more components of sound processor 504 may be configured to perform any of the functions described in connection with FIG. 9.

As shown in FIG. 9, current steering may be applied to two or more electrodes 514 (e.g., electrodes 514-1 and 514-2). Two electrodes 514 are shown in FIG. 9 for illustrative purposes only. It will be recognized that current steering may alternatively be applied to three or more electrodes as may serve a particular application. Electrodes 514-1 and 514-2 may be adjacent one to another (i.e., no other electrode 514 is physically disposed in between them on lead 512). Alternatively, electrodes 514-1 and 514-2 may be non-adjacent (i.e., one or more electrodes 514 are physically disposed in between them on lead 512).

As shown in FIG. 9, an input signal may be filtered by at least one filter 902 configured to generate a frequency domain signal representative of a distinct frequency portion of the audio signal. The input signal is also input into a frequency estimator 904 configured to estimate the peak frequency thereof. A time pattern block 906 is configured to build construct the temporal structure of a pulse train representing the signal output by the at least one filter 902. Mapping modules 908 are configured to map the amplitude of the signal output by the time pattern block 906 to corresponding current levels in accordance with a suitable mapping function.

The output of each mapping module 908 is input into a current steering module 910. The current steering module 910 is also configured to receive the output of the frequency estimator 904. In some examples, the current steering module 910 is configured to determine appropriate weighting factors for current to be applied to electrodes 514-1 and 514-2. This determination may be based at least in part on the peak frequency estimate and the output of each of the mapping modules 908. The weighting factors may be applied to the current using multiplication blocks 912. In this manner, stimulation current may be delivered to a stimulation site located in between areas associated with electrodes 514-1 and 514-2.

Figure 10:
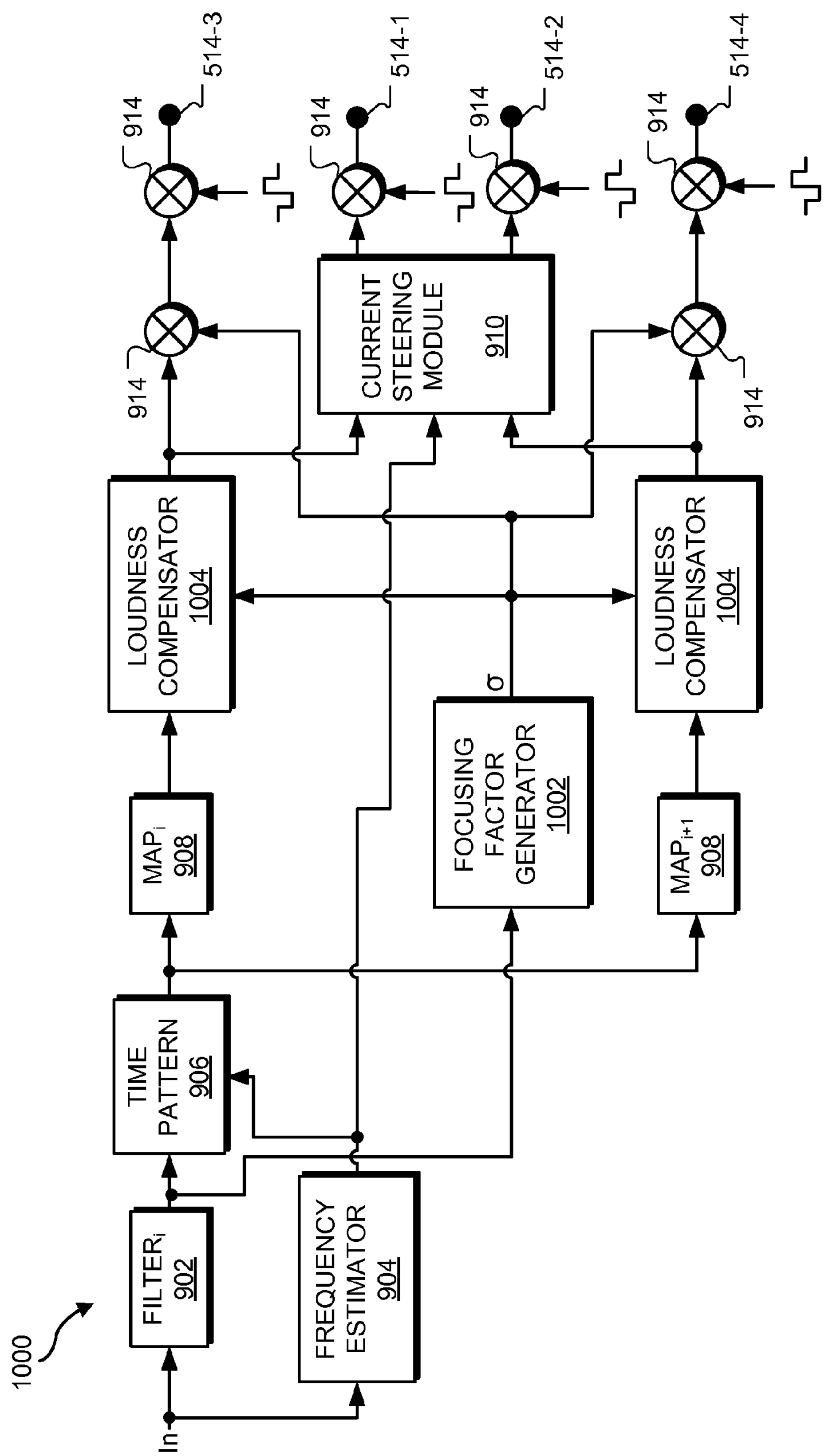
FIG. 10 illustrates another exemplary implementation of a current steering strategy according to principles described herein.

The excitation field produced by the current steering electrodes 514-1 and 514-2 may be narrowed by applying compensating current simultaneously via one or more additional electrodes. FIG. 10 illustrates another exemplary implementation 1000 of a current steering strategy that may be used to dynamically focus one or more excitation fields produced by current steering electrodes (e.g., electrodes 514-1 and 514-2). The components and functions illustrated in FIG. 10 may be implemented by any of the subsystems, facilities, and/or modules described herein. For examples, one or more components of sound processor 504 may be configured to perform any of the functions described in connection with FIG. 10.

Implementation 1000 includes many of the same components as the implementation described in connection with FIG. 9. In addition, functional block diagram 1000 includes a focusing factor generator 1002 configured to generate a focusing factor σ based on the amplitude of the signal output by filter 902. The focusing factor σ is used to generate scaled versions of the current steering current. This scaled current is delivered via one or more additional electrodes (e.g., electrodes 514-3 and 514-4) to effectively narrow the excitation field produced by electrodes 514-1 and 514-2.

As shown in FIG. 10, loudness compensators 1004 may also be included within the implementation 1000 of FIG. 10. Loudness compensators 1004 are configured to adjust the amplitudes of the currents applied via electrodes 514-1 and 514-2 to compensate for loudness changes that may be caused by current delivered via the compensating electrodes 514-3 and 514-4.

While exemplary implementations 900 and 1000 of a current steering stimulation strategy have been described herein, it will be recognized that other implementations of a current steering stimulation strategy may additionally or alternatively used as may serve a particular application.

In some examples, stimulation strategy module 618 may additionally or alternatively generate one or more stimulation parameters in accordance with an N-of-M stimulation strategy. As mentioned, an N-of-M stimulation strategy is one in which stimulation current is only applied to N of M total stimulation channels during a particular stimulation frame, where N is less than M. To this end, stimulation strategy module 618 may include one or more components configured to select the N stimulation channels to which stimulation is to be applied. Stimulation strategy module 618 may be configured to perform this selection in accordance with any suitable selection heuristic. For example, the N stimulation channels may correspond to noise reduced frequency domain signals that have the highest energy levels, contain the most relevant information, and/or have any other desirable characteristic as may serve a particular application. Other heuristics may be used to determine the N stimulation channels as may serve a particular application.

As detailed above, the methods and systems described herein facilitate reduction of an effect of ambient noise within an auditory prosthesis system. As an example, an exemplary method includes dividing an audio signal presented to an auditory prosthesis patient into a plurality of analysis channels each containing a frequency domain signal representative of a distinct frequency portion of the audio signal, determining a noise reduction gain parameter for each of the frequency domain signals, applying noise reduction to the frequency domain signals in accordance with the determined noise reduction gain parameters to generate a noise reduced frequency domain signal corresponding to each of the analysis channels, and generating one or more stimulation parameters based on the noise reduced frequency domain signals and in accordance with at least one of a current steering stimulation strategy and an N-of-M stimulation strategy.

An exemplary system includes a frequency analysis facility configured to a divide an audio signal presented to an auditory prosthesis patient into a plurality of analysis channels each containing a frequency domain signal representative of a distinct frequency portion of the audio signal, a noise reduction facility communicatively coupled to the analysis channel facility and configured to determine a noise reduction gain parameter for each of the frequency domain signals and apply noise reduction to the frequency domain signals in accordance with the determined noise reduction gain parameters to generate a noise reduced frequency domain signal corresponding to each of the analysis channels, and a stimulation strategy facility communicatively coupled to the noise reduction facility and configured to generate one or more stimulation parameters based on the noise reduced frequency domain signals and in accordance with at least one of a current steering stimulation strategy and an N-of-M stimulation strategy.

Another exemplary system includes a sound processor communicatively coupled to an implantable cochlear stimulator. The sound processor is configured to divide an audio signal presented to an auditory prosthesis patient into a plurality of analysis channels each containing a frequency domain signal representative of a distinct frequency portion of the audio signal, determine a signal-to-noise ratio and a noise reduction gain parameter based on the signal-to-noise ratio for each of the frequency domain sign, and apply noise reduction to the frequency domain signals in accordance with the determined noise reduction gain parameters to generate a noise reduced frequency domain signal corresponding to each of the analysis channels. The implantable cochlear stimulator is configured to generate electrical stimulation based on the noise reduced frequency domain signals and apply the electrical stimulation to at least one stimulation site within a cochlea of a patient via a plurality of stimulation channels in accordance with at least one of a current steering stimulation strategy and an N-of-M stimulation strategy.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method of reducing an effect of ambient noise within an auditory prosthesis system, the method comprising:

dividing, by a sound processing subsystem, an audio signal presented to an auditory prosthesis patient into a plurality of analysis channels each containing a frequency domain signal representative of a distinct frequency portion of the audio signal;

determining, by the sound processing subsystem, a noise reduction gain parameter for each of the frequency domain signals based on a signal-to-noise ratio of each of the frequency domain signals;

applying, by the sound processing subsystem, noise reduction to the frequency domain signals in accordance with the determined noise reduction gain parameters to generate a noise reduced frequency domain signal corresponding to each of the analysis channels; and generating, by the sound processing subsystem, one or more stimulation parameters based on the noise reduced frequency domain signals and in accordance with at least one of a current steering stimulation strategy and an N-of-M stimulation strategy.

2. The method of claim 1, further comprising generating and applying, by a stimulation subsystem communicatively coupled to the sound processing subsystem, electrical stimulation to at least one stimulation site associated with an auditory pathway of a patient via one or more of a plurality of stimulation channels in accordance with the one or more stimulation parameters.

3. The method of claim 2, wherein a total number of the plurality of stimulation channels is greater than or equal to a total number of the analysis channels.

4. The method of claim 1, further comprising dynamically adjusting, by the sound processing subsystem, an amount of the noise reduction applied to the frequency domain signals in accordance with a type of the audio signal.

5. The method of claim 4, wherein when the audio signal comprises music, the dynamically adjusting comprises reducing the amount of the noise reduction applied to the frequency domain signals.

6. The method of claim 1, wherein the determining of the noise reduction gain parameter for each of the frequency domain signals comprises:

determining the signal-to-noise ratio for each of the frequency domain signals.

7. The method of claim 6, wherein the if the signal-to-noise ratio of a frequency domain signal included within the frequency domain signals is greater than a predetermined maximum threshold, the determining of the noise reduction gain parameter corresponding to the frequency domain signal comprises assigning a value of one to the noise reduction gain parameter corresponding to the frequency domain signal.

8. The method of claim 7, further comprising independently setting the predetermined maximum threshold.

9. The method of claim 6, wherein the if the signal-to-noise ratio of a frequency domain signal included within the frequency domain signals is less than a predetermined minimum threshold, the determining of the noise reduction gain parameter corresponding to the frequency domain signal comprises assigning a value of zero to the noise reduction gain parameter corresponding to the frequency domain signal.

10. The method of claim 1, wherein the generating of the one or more stimulation parameters is in accordance with the current steering stimulation strategy, and wherein the method further comprises generating, by the sound processing subsystem, a focusing factor used to narrow one or more excitation fields produced by the current steering stimulation strategy.

11. The method of claim 1, wherein the generating of the one or more stimulation parameters is in accordance with the N-of-M stimulation strategy, and wherein the method further comprises selecting, by the sound processing subsystem, N stimulation channels to which electrical stimulation is to be applied in accordance with a selection heuristic.

12. A system comprising:

a frequency analysis facility configured to a divide an audio signal presented to an auditory prosthesis patient into a plurality of analysis channels each containing a frequency domain signal representative of a distinct frequency portion of the audio signal;

a noise reduction facility communicatively coupled to the frequency analysis facility and configured to determine a noise reduction gain parameter for each of the frequency domain signals based on a signal-to-noise ratio of each of the frequency domain signals, and apply noise reduction to the frequency domain signals in accordance with the determined noise reduction gain parameters to generate a noise reduced frequency domain signal corresponding to each of the analysis channels; and a stimulation strategy facility communicatively coupled to the noise reduction facility and configured to generate one or more stimulation parameters based on the noise reduced frequency domain signals and in accordance with at least one of a current steering stimulation strategy and an N-of-M stimulation strategy.

13. The system of claim 12, further comprising:

a current generation facility configured to generate electrical stimulation in accordance with the one or more stimulation parameters; and a stimulation facility configured to apply the electrical stimulation to at least one stimulation site associated with an auditory pathway of a patient via one or more of a plurality of stimulation channels in accordance with the one or more stimulation parameters.

14. The system of claim 13, wherein a total number of the plurality of stimulation channels is greater than or equal to a total number of the analysis channels.

15. The system of claim 12, wherein the noise reduction facility is further configured to dynamically adjust an amount of the noise reduction applied to the frequency domain signals in accordance with a type of the audio signal.

16. The system of claim 15, wherein when the audio signal comprises music, the noise reduction facility is configured to dynamically adjust the amount of noise reduction applied to the frequency domain signals by reducing the amount of the noise reduction applied to the frequency domain signals.

17. The system of claim 12, wherein if a signal-to-noise ratio of a frequency domain signal included within the frequency domain signals is greater than a predetermined maximum threshold, the noise reduction facility is further configured to assign a value of one to a noise reduction gain parameter corresponding to the frequency domain signal.

18. The system of claim 12, wherein if a signal-to-noise ratio of a frequency domain signal included within the frequency domain signals is less than a predetermined minimum threshold, the noise reduction facility is further configured to assign a value of zero to a noise reduction gain parameter corresponding to the frequency domain signal.

19. The system of claim 12, wherein the generating of the one or more stimulation parameters is in accordance with the current steering stimulation strategy, and wherein the stimulation strategy facility is further configured to generate a focusing factor used to narrow one or more excitation fields produced by the current steering stimulation strategy.

20. A system comprising:

a sound processor configured to divide an audio signal presented to an auditory prosthesis patient into a plurality of analysis channels each containing a frequency domain signal representative of a distinct frequency portion of the audio signal, determine a signal-to-noise ratio and a noise reduction gain parameter based on the signal-to-noise ratio for each of the frequency domain signals, and apply noise reduction to the frequency domain signals in accordance with the determined noise reduction gain parameters to generate a noise reduced frequency domain signal corresponding to each of the analysis channels; and an implantable cochlear stimulator communicatively coupled to the sound processor and configured to generate electrical stimulation based on the noise reduced frequency domain signals, and apply the electrical stimulation to at least one stimulation site within a cochlea of a patient via a plurality of stimulation channels in accordance with at least one of a current steering stimulation strategy and an N-of-M stimulation strategy.

* * * * *